(12) United States Patent
Duishoev et al.

(10) Patent No.: US 11,210,346 B2
(45) Date of Patent: Dec. 28, 2021

(54) PREDICTIVE SYSTEM FOR GENERATING CLINICAL QUERIES

(71) Applicant: IQVIA Inc., Parsippany, NJ (US)

(72) Inventors: Nurlanbek Duishoev, Frankfurt am Main (DE); Kristy Morgan, Chapel Hill, NC (US); Joaquin Palancar Arbona, Madrid (ES); Lucas Glass, Devon, PA (US); Shyam Sakhrani, London (GB)

(73) Assignee: IQVIA Inc., Parsippany, NJ (US)

( * ) Notice: Subject to any disclaimer, the term of this patent is extended or adjusted under 35 U.S.C. 154(b) by 145 days.

(21) Appl. No.: 16/375,403

(22) Filed: Apr. 4, 2019

(65) Prior Publication Data
US 2020/0320139 A1    Oct. 8, 2020

(51) Int. Cl.
*G06F 16/903* (2019.01)
*G06N 5/02* (2006.01)
(Continued)

(52) U.S. Cl.
CPC ...... *G06F 16/90335* (2019.01); *G06F 16/353* (2019.01); *G06F 16/383* (2019.01); *G06N 5/02* (2013.01)

(58) Field of Classification Search
CPC .... G06F 16/30; G06F 16/3322; G06F 16/353; G06F 16/355; G06F 16/38; G06F 16/383; G06F 16/90335; G06N 5/02
See application file for complete search history.

(56) References Cited

U.S. PATENT DOCUMENTS 10,140,421 B1* 11/2018 Bernard ............... G06F 40/279
2009/0076839 A1* 3/2009 Abraham-Fuchs .... G16H 70/60
705/2
(Continued)

FOREIGN PATENT DOCUMENTS

EP          2985711          2/2016

OTHER PUBLICATIONS

Friedman et al. "Automated Encoding of Clinical Documents Based on Natural Language Processing", Journal of the American Medical Informatics Association, vol. 11, Issue 5, Sep. 2004, pp. 392-402, https://doi.org/10.1197/jamia.M1552 (Year: 2004).*
(Continued)

*Primary Examiner* — James E Richardson
(74) *Attorney, Agent, or Firm* — Fish & Richardson P.C.

(57) ABSTRACT

Methods, systems, and apparatus, including computer programs encoded on a computer storage medium, for generating a predictive system that obtains and processes data describing terms for different medical concepts to generate commands from a user query. An entity module of the system determines whether a term describes a medical entity associated with a healthcare condition affecting an individual. When the term describes the medical entity an encoding module links the medical entity with a specified category based on an encoding scheme. The system receives the user query. A parsing engine of the system uses the received query to generate a machine-readable command by parsing the query against terms that describe the medical entity and based on the encoding scheme for linking the medical entity to the specified category. The system uses the command to query different databases to obtain data for generating a response to the received query.

20 Claims, 5 Drawing Sheets

(51) Int. Cl.
*G06F 16/383* (2019.01)
*G06F 16/35* (2019.01)

(56) References Cited

U.S. PATENT DOCUMENTS

| | | |
|---|---|---|
| 2009/0083218 A1 | 3/2009 | Rejndrup |
| 2013/0066870 A1* | 3/2013 | Somasundaran ....... G06F 16/35 707/737 |
| 2015/0095016 A1 | 4/2015 | Karres et al. |
| 2015/0178386 A1* | 6/2015 | Oberkampf ............ G16H 15/00 707/749 |
| 2015/0379241 A1 | 12/2015 | Furst et al. |
| 2016/0019299 A1* | 1/2016 | Boloor ................... G06F 16/36 705/3 |
| 2016/0048655 A1* | 2/2016 | Maitra ................... G16H 20/10 705/3 |
| 2017/0199963 A1* | 7/2017 | Kondadadi ............ G06Q 10/10 |
| 2018/0025121 A1 | 1/2018 | Fei et al. |
| 2018/0075192 A1* | 3/2018 | Sethumadhavan ..... G06F 16/21 |
| 2019/0163875 A1* | 5/2019 | Allen ..................... G16H 50/70 |

OTHER PUBLICATIONS

Kundeti et al. "Clinical named entity recognition: Challenges and opportunities," 2016 IEEE International Conference on Big Data (Big Data), 2016, pp. 1937-1945, doi: 10.1109/BigData.2016.7840814 (Year: 2016).*

Gudivada et al. "A Literature Review on Machine Learning Based Medical Information Retrieval Systems," 2018 IEEE Symposium Series on Computational Intelligence (SSCI), 2018, pp. 250-257, doi: 10.1109/SSCI.2018.8628846. (Year: 2018).*

EP Search Report and Written Opinion in European Application No. EP20168239, dated Aug. 25, 2020, 10 pages.

\* cited by examiner

PREDICTIVE SYSTEM FOR GENERATING CLINICAL QUERIES

FIELD

This specification relates to predictive computing systems.

BACKGROUND

As part of the healthcare process, physicians or other medical care providers may perform clinical trials, programs, and other activities to evaluate subject safety and efficacy of a pharmaceutical drug or other medical treatment option. The use of health-related trial programs can help to identify novel treatment options for improving overall patient health and reducing health system costs. A clinical trial or program can be a single research study or multiple research studies that prospectively assigns human participants/subjects or groups of human subjects to one or more health-related interventions to evaluate the effects on health outcomes.

SUMMARY

As part of the healthcare process, physicians or other medical care providers may perform trials, programs, and other activities to evaluate the efficacy of a particular pharmaceutical drug or other medical treatment option. Conducting health-related clinical trials can help to identify medical treatment options for improving overall patient health and reducing health system costs. Clinical trials and other controlled programs are generally conducted by one or more investigators at medical facilities in different geographic locations that interact with study subjects to evaluate the efficacy of a drug treatment option. In some instances a physician for a patient can be associated with a clinical trial and the physician can refer a patient as a candidate for participation in a trial based on a diagnosed condition of the patient. An investigator, a geographic location, or both, can form an entity that executes a program.

Based on the above context, this document describes a computing system that uses specific computing rules or instructions (e.g., a unique algorithm) to predict or generate commands based on a received user input. To generate the commands, the system is configured to train a predictive model using one or more learning algorithms (e.g., deep learning algorithms). The predictive model is used to process terms that are recognized and extracted using a natural language processor (NLP) in an entity module of the system. The predictive model can be trained to semantically understand relevant terms (e.g., medical and clinical terms) and their relations to other medical terms. Terms can be extracted from information sources such as textbooks and online resources, or from unstructured datasets such as electronic medical data for multiple healthcare patients.

An encoding module uses one or more neural network models to encode and link the extracted terms to a particular medical entity, such as a disease entity, a drug entity, a medical procedure entity, or various other types of entities. The system leverages the predictive model's learned inferences about the encoded medical terms to generate a command based on a received query from a user. For example, a parsing engine can automatically translate the extracted terms into a machine-readable command that is processed against a medical database to obtain an accurate response to the user query. Hence, at least one goal of the predictive system is to accurately interpret, in a manner that is computationally efficient, a user query that includes health-related information about a patient or set of patients.

For example, the user query represents user input, to the predictive system, that specifies a list(s) of patient attributes. The query/user input can be in a human-readable format. The described techniques enable the system to quickly and efficiently generate a corresponding command in a computer-readable format. The computer-readable command is then used to query different electronic health records (EHR) to identify patients (e.g., trial subjects) that satisfy a given condition(s) based on the attributes specified in the list. For example, the command can be used to query historical medical records to derive insights and information without manual intervention (e.g., from a human-operator). The derived insights can include accurate estimation of an eligible patient population for clinical trial participation and estimation of a propensity for adverse events).

One aspect of the subject matter described in this specification can be embodied in a computer-implemented method that includes: obtaining a first set of data including multiple terms; determining that a term of the multiple terms describes a medical entity; responsive to determining that the term describes the medical entity, linking the medical entity with a category based on an encoding scheme for the category; responsive to receiving a query, generating a machine-readable command by parsing the query against terms in the first set of data that describe the medical entity and based on the encoding scheme; using the machine-readable command to query multiple databases; obtaining a second set of data responsive to the received query when the machine-readable command is used to query the multiple databases; and providing the second set of data as an output for display at a user device.

These and other implementations can each optionally include one or more of the following features. For example, in some implementations, determining whether a term describes the medical entity includes: generating a confidence score based on inferences of similarity between terms described in the first set of data and the medical entity; and determining the confidence score exceeds a threshold confidence score.

In some implementations, linking the medical entity with the category includes: obtaining a listing of category codes for the category; determining a match between the term and corresponding category codes in the listing of category codes; and linking the medical entity with the specified category based on the match between the term that describes the medical entity and the corresponding category codes.

In some implementations, linking the medical entity with the category includes: encoding the medical entity with corresponding category codes based on the encoding scheme for the specified category; and the encoding scheme for the specified category is a hierarchical encoding scheme including a hierarchy of levels.

In some implementations, encoding the medical entity with corresponding category codes includes: quantifying content including the medical entity to be encoded; determining depths of levels in the hierarchy of levels for mapping the content; and associating the medical entity included in the content with the corresponding category codes for a particular depth level in the hierarchy of levels.

In some implementations, the medical entity is a disease, and determining the match includes: generating a respective match score for each level in the hierarchy of levels; and determining that the respective match score exceeds a threshold match score.

In some implementations, determining that the term describes the medical entity includes: performing a lookup of the term against information in an entity-specific dataset; and determining that the term describes the medical entity based on a match between the term and a first entry in the entity-specific dataset.

In some implementations, the medical entity is associated with a healthcare condition that affects an individual, and the medical entity includes at least one of: one or more medical diseases; medical drugs for treating the one or more medical diseases; medical procedures associated with the one or more medical diseases; or data describing multiple medical findings that correspond to a healthcare condition of the individual.

In some implementations, the entity specific dataset is generated based on data including at least one of: i) a predefined set of information describing multiple diseases; ii) a predefined set of information describing multiple drugs; iii) a predefined set of information describing multiple medical procedures; or iv) electronic medical data for multiple healthcare patients.

In some implementations, obtaining the data that describes the terms relating to the multiple medical concepts includes: obtaining multiple unstructured data; and structuring the unstructured data to enable processing of the query against information in the multiple databases.

Other implementations of this and other aspects include corresponding systems, apparatus, and computer programs, configured to perform the actions of the methods, encoded on computer storage devices. A computing system of one or more computers or hardware circuits can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The subject matter described in this specification can be implemented to realize one or more of the following advantages. The described techniques provide a scalable computing system that is a fully automated end-to-end predictive solution for analyzing and parsing structured and unstructured datasets. Using the analyzing and parsing functions, a predictive model of the system is configured such that information in the datasets can be queried using a machine-readable command that is generated based on data inferences learned by the predictive model.

The predictive system is configured to quickly and efficiently analyze multiple datasets that describe a variety of diseases and indications, drugs/treatment options, and medical procedures. For example, the efficiency of the system is evidenced by the use of three steps to generate the command: (1) extraction of entities that describe patient attributes; (2) mapping a condition to a standardized scientific entity name; and (3) interpreting relationships between different healthcare conditions, including whether the conditions are negated or not.

Hence, the system provides a solution that specializes in recognizing and encoding medical language terms and requires little (or no) manual data curation to achieve a desired level of accuracy in the commands or machine-readable queries that are generated and processed to obtain a response to user input. The predictive system uses learning algorithms (e.g., deep learning algorithms) to determine relationships between relevant categories of information and uses the relations between the information categories to directly query medical and research databases.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Current systems store medical information in an unstructured data format and the information may be dispersed across several systems, which makes it difficult for the information to be queried and linked to other data sources. Many sources of this medical information are text based sources and the information can be formed from different elements. However, there is no international or existing categorization of these different elements that is widely followed.

When querying information from these medical sources, domain expertise is often required to recognize relevant terms, categorize the terms, and convert the terms to a suitable format that can be used to query data. The ability to model and structure this medical information enable users to derive certain insights that can improve health conditions for a set of patients. For example, at least one use can involve querying a patient database to accurately calculate a patient pool with health attributes that meet the protocols and criteria for participation in a new clinical trial.

In this context, techniques are described for generating a predictive model that extracts and semantically understands relevant clinical terms and a relationship between the terms. A computing system is used to extract the clinical terms from structured and unstructured datasets, e.g., using natural language processing (NLP) and deep learning algorithms. The techniques use data processing modules to recognize, extract, and categorize medical entities (e.g., indications, drugs, procedures, etc.) as well as determine relationships between the medical entities with reference to the terms that describe the entities.

The information obtained from these processes is used to generate a machine-readable command for querying different databases to derive various insights and information about a set of patients without manual user intervention. For example, the command can be used to query databases of historical medical records to obtain an estimate of eligible patient populations for participation in clinical trials or to obtain an estimate of a propensity for the occurrence of adverse events in connection with a clinical trial.

Figure 1:
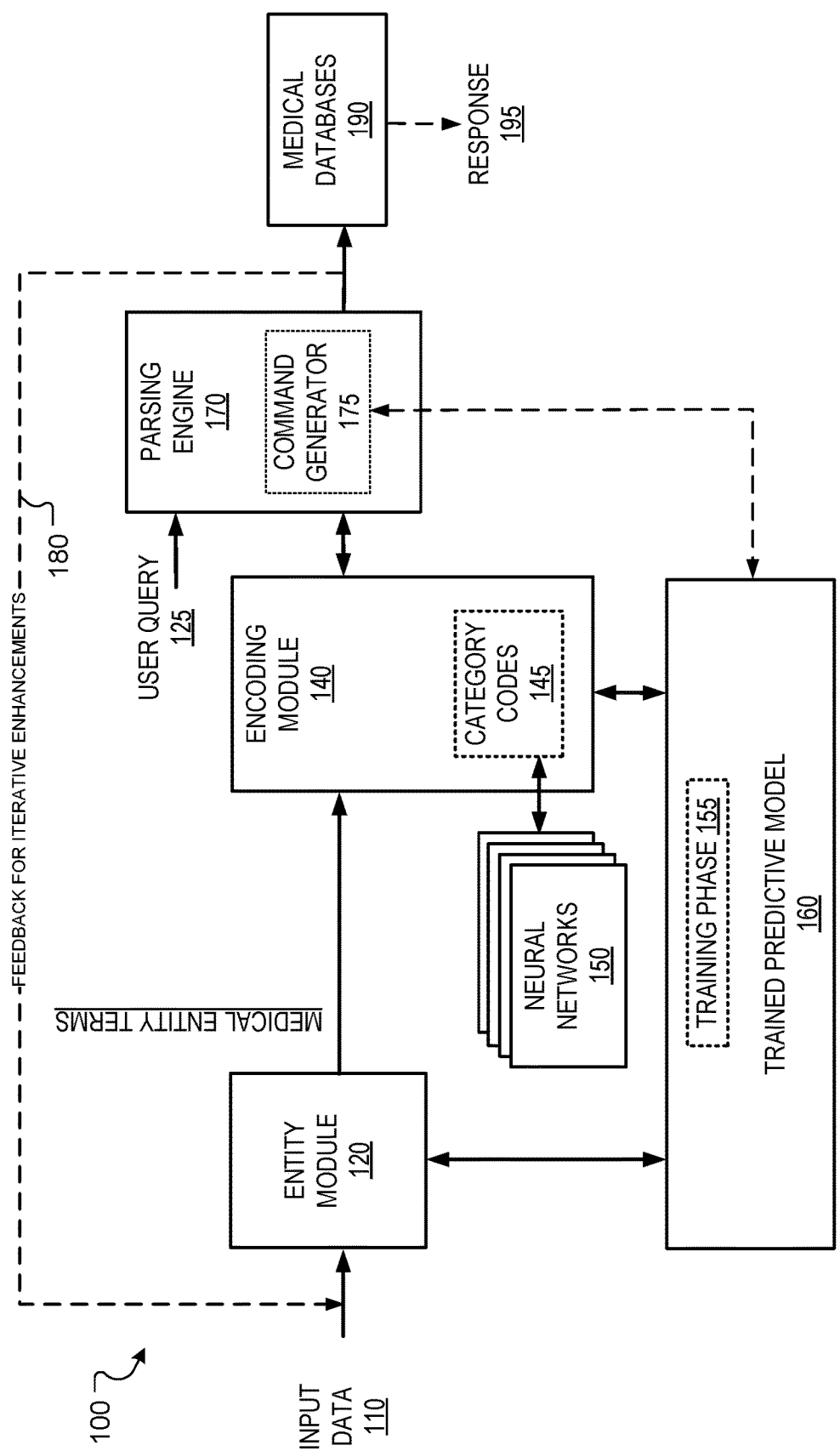
FIG. 1 shows a block diagram of an example computing system for generating machine-readable commands.

FIG. 1 shows a block diagram of an example computing system 100 for detecting undiagnosed conditions. System 100 can be a predictive computing system configured to process input data to train a predictive model. As described herein, the predictive model is trained to perform various functions related to processing and semantically understanding relevant clinical and medical terms.

System 100 includes an entity module 120, an encoding module 140, a predictive model 160, and a parsing engine 170. During an example training phase 155, the entity module 120 and encoding module 140 are used to process input data 110 to compute learned inferences for generating a trained predictive model 160. Hence, the training phase 155 is associated with an example predictive model and is performed at system 100 to train and generate the predictive model 160.

As described herein, the trained predictive model 160 is configured to extract and semantically understands relevant clinical terms and their relations from a variety of input text. The predictive model is used to process terms that are recognized and extracted using a natural language processor (NLP) in an entity module of the system. System 100 leverages the predictive model's learned inferences about the encoded medical terms to generate a command based on a received query from a user.

In general, system 100 obtains or receives input data 110 for processing at the system. The input data 110 can include structured and unstructured data. The structured data can include various types of publications and health-related text, such as medical textbooks, online publications relating to healthcare, medical journals, electronic publications, medical treatises, web-based articles, medical websites, or various resources of information that is inherently formatted for data extraction and processing by a computer system. The unstructured data may include different datasets relating to medical activities, patient medical records, or healthcare transactions, and is described in detail below with reference to at least FIG. 2.

Entity module 120 is configured to receive or obtain the input data 110 and process the data for training one or more predictive models of system 100. In some implementations, entity module 120 is a name entity recognition (NER) module that executes a high-level general-purpose programming language to recognize and extract data elements from input data 110. For example, entity module 120 can be a python module that uses coded instructions to identify terms and words (data elements) that describe medical entities for different medical concepts in a document. The document can be an electronic document, such as a digital version of a medical text book, and the terms or words can describe medical entities, such as disease names, drug therapies, drug compound, or medical procedures.

As described in more detail below with reference to FIG. 2, entity module 120 includes various data searching/lookup and a machine-learning functions. These functions can be used to perform a dictionary look-up of each word or term in a medical document or structured data source included in the input data 110. In some implementations, the lookup functions and machine-learning functions are independent computing functions of the entity module 120. As described in more detail below, each computing function can be used to determine whether terms or data elements in the input data 110 describe particular medical entities.

For example, each word or term in a medical document of the input data 110 is searched against a curated data source, such as a dictionary of entity-specific medical terms. In some implementations, performing the dictionary lookup includes extracting one or more n-grams from the medical document that are recognized as matching one or more terms in the curated data source. The extracted n-grams can include contiguous data items or elements, e.g., letters or words, which match terms in the curated data source. For example, the medical document can have letters that form words that describe a particular medical condition, such as cancer. The extracted n-grams can include contiguous letters or words that match terms in the curated data source that also describe different medical concepts related to cancer.

Encoding module 140 is configured to receive or obtain data associated with medical entities, where the data includes corresponding terms that describe the medical entities. The encoding module 140 encodes the data associated with the medical entities and the encoded data is used for training one or more predictive models of system 100. In some implementations, encoding module 140 is a multi-purpose encoding module that executes a high-level general-purpose programming language to encode the data associated with the medical entities. In some cases, much like entity module 120, encoding module 140 can also be a python module that uses coded instructions to perform various functions.

Encoding module 140 can use the instructions to link, associate, or otherwise encode medical entities with a specified category code 145 in response to the entity module 120 determining that a term describes the medical entity. For example, encoding module 140 encodes medical entities into a specified entity organization, where i) diseases can be encoded based on ICD-10 codes, ii) drugs can be encoded based on GPI codes, and iii) procedures can be encoded based on PRC_CD codes. The ICD-10 codes, GPI codes, and PRC_CD codes are each associated with a respective encoding scheme for health-related diseases, pharmaceutical drugs, and medical procedures.

As described in more detail below, medical entities are linked or encoded with a specified category code 145 based on an encoding scheme for the specified category. In some implementations, each identified or extracted medical entity is encoded to a particular nomenclature (e.g., official disease name and corresponding category code). In some cases, one or more medical entities are encoded to more than one nomenclature. For example, drugs can be encoded at least to a particular GPI code, to a particular ATC code, or to both.

Encoding module 140 can include discrete computing elements that are each used to perform the respective encoding operation for either diseases, drugs, or procedures. In some implementations, at least with reference to encoding medical entities for health-related diseases, the encoding scheme for the category codes 145 is a hierarchical encoding scheme that is based on a hierarchy of levels (or depth levels). In this manner, encoding a medical entity for health-related diseases with a corresponding category code 145 includes determining depths of levels in the hierarchy of levels and determining the appropriate level for mapping certain information content that includes the data associated with the medical entity.

One or more neural networks 150 can be used to determine the depths of levels in the hierarchy of levels and to determine the corresponding level for mapping the data associated with the medical entity. The encoding module 140 can use an output (e.g., a computed inference or confidence score) of the neural networks 150 to associate the medical entity included in the information content with the corresponding category code 145 for a particular depth level in the hierarchy of levels. For example, one or more scores that each represent an inference output of each respective neural network 150 may be used to associate the medical entity with a particular depth level in the hierarchy of levels and a corresponding one or more category codes 145 at that particular depth level.

Parsing engine 170 is a semantic query parser that is configured to convert user input 125 to a machine-readable command. For example, user input 125 can represent a human-understandable query and a command generator 175 is configured to generate the machine-readable command based on one or more query parsing operations that are performed on the user input 125. The parsing engine 170 uses the command generator 175 to generate the machine-readable command in response to converting the user input 125 to machine-commands based on results of the one or more query parsing operations.

The generated commands can represent machine-understandable queries that are configured for processing against different medical or informational databases 190. Parsing engine 170 performs the query parsing operations to translate recognized entity relations into commands. In addition to recognizing entities, parsing engine 170 can perform the query parsing operations to determine types of relationships between terms based on certain keywords in the user input 125, a certain position of words in the text of the user input 125, or semantic attributes of terms that form the user input 125.

The commands are associated with logic operations that are understandable and executable by computers. The commands and logic operations can cause the computers to query a particular dataset of databases 190, which may include executing filters or joins on tables of a relational database to obtain data elements for generating a response 195. In some implementations, the generated commands can have a machine-readable format, such as a query format that is based on the structured query language (SQL). In some implementations, a command may be formatted as an SQL query and used to obtain or manage data stored in an example relational database 190, or for streaming data processing in a relational data stream management system.

An example use case for system 100 includes receiving entity module 120 receiving data specifying a protocol for a new clinical trial. Entity module 120 is used to recognize all relevant medical entities included in the protocol based on identifying and extracting one or more terms that describe entities. The encoding module 140 categorizes each of the recognized medical entities using the one or more extracted terms for each entity. For example, the parsing engine module 170 can categorize the entities as inclusion or exclusion criteria for obtaining subjects that can participate in the new clinical trial. The command generator 175 of the parsing engine 170 writes or generates a command (e.g., a query) that integrates the entities. The machine-readable command can also account for how each medical entity, and their associated terms, are related.

The command is run or processed against a given dataset in a database, e.g., a medical transactions database. System 100 generates a result in response to processing the command against the database. The result can be a number of patients or potential trial subjects with medical attributes that satisfy the inclusion and exclusion criteria for the new clinical trial. As used in this document, a subject or trial subject may be a candidate for participation in a clinical trial, a participant in a clinical trial, or an existing patient (of a healthcare provider) that may be identified for participation in a clinical trial.

System 100 can be configured to improve or enhance accuracy of the output determinations that are generated using at least the predictive model 160. For example, system 100 includes a feedback loop 180 that enables certain output determinations to be fed back as inputs to system 100. The feedback loop 180 can ensure full capture of discrete parameters in a set of input data 110 processed by at least the entity module 120 and encoding module 140. By feeding back data parameters of an output, such as a generated command or computed inference determination, the feedback loop 180 can be used to improve or enhance an accuracy of the predictive model 160.

For example, using the feedback loop 180, system 100 can iteratively enhance its prediction capabilities by detecting new relationships and commonalities that may exist among a more granular set of parameters in an output. In some cases, system 100 obtains this iterative enhancement in accuracy in response to reevaluating output data that may include certain determinations about relationships among terms or data elements that describe different medical entities. System 100 can use the feedback loop 180 along with the entity module 120 and encoding module 140 to jointly and iteratively process various types of input data 110, including the feedback data, with reduced computation cost and better accuracy relative to conventional systems.

In some implementations, an example training phase 155 of system 100 can be based on the feedback loop 180, in which embedded vectors (outputs) are fed back to the system 100 as inputs to the system that are then analyzed to iteratively enhance the accuracy of the outputs and determinations generated by the predictive model 160. In other implementations, in addition to the feedback loop 180, system 100 is configured to expand a current list of different medical entities that can be recognized using the computing rules (e.g., algorithms) executed by the modules and computing elements of the system.

Figure 2:
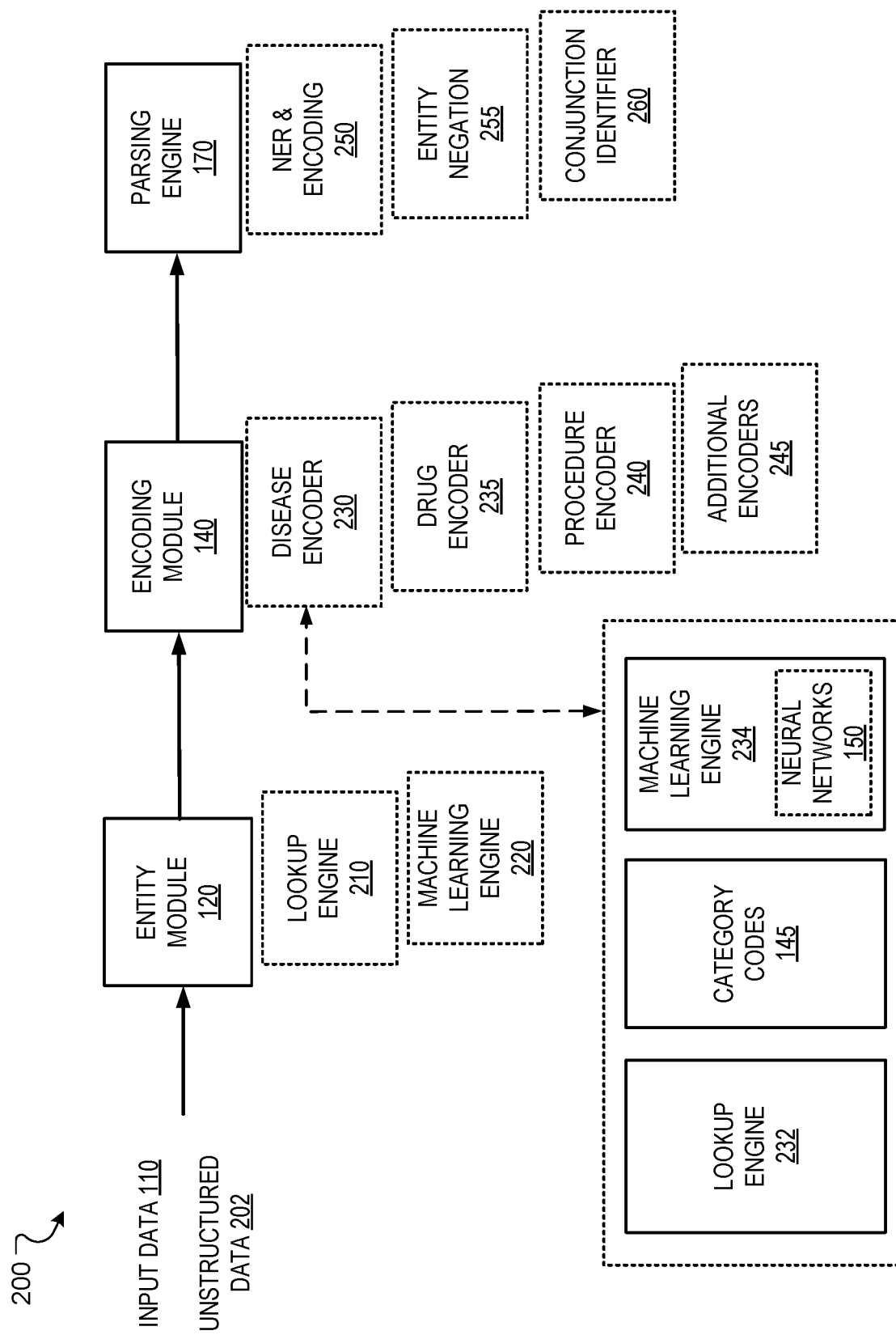
FIG. 2 shows a block diagram of example data processing modules of the computing system of FIG. 1.

FIG. 2 shows a block diagram of example data processing modules 200 that correspond to the modules of system 100 described above with reference to FIG. 1. As shown at the implementation of FIG. 2, the data processing modules 200 of system 100 can include additional computing elements. These additional computing elements can represent subsystems of the respective modules 120, 140, and 170 that are described above. For example, the additional elements can perform computing functions for processing input data during an example training phase of system 100 to generate the trained predictive model 160.

As indicated above, the input data 110 processed during training phase 155 includes structured and unstructured data. For example, unstructured data 202 can include information describing health and medical attributes for a large set of patients or subjects. Unstructured data 202 can also include information describing sponsorship and execution details for a set of clinical trials. The execution details can specify information such as the medical facility, geographic location, and investigator(s) for each trial, as well as the inclusion and exclusion criteria for each trial in a set of clinical trials.

In some cases, unstructured data 202 includes multiple respective datasets of healthcare transaction information and multiple respective datasets of demographic information for individual patients or prospective subjects. The healthcare transaction information can be obtained from data describing interactions between physicians and patients, data derived from a subject's physical or electronic medical records (EMR), data derived from prescription records/medical claims ("Rx/Dx data"), data relating to prescriptions or treatment options used by a patient or subject, or from other data sources relating to healthcare transactions and healthcare activities. The demographic information may include a patient identification number, a subject's age, a subject's gender and/or preferred pronoun, a subject's geographic region or address location, as well as other identifying data about a person.

Entity module 120 uses coded instructions, e.g., instructions based on the python programming language, to identify medical concepts in a document and perform named entity recognition. As noted above, entity module 120 includes various data searching/lookup and a machine-learning functions. In particular, entity module 120 includes a data lookup engine 210 and a machine-learning engine 220. In some implementations, the lookup engine 210 and machine-learning engine 220 are independent computing elements of the entity module 120. Each of engines 212, 220 are configured to recognize certain data elements in the input data 110 and extract or label the data elements as describing, or being associated with, particular medical entities.

Lookup engine 210 is configured to perform dictionary lookups of each term or word in the input data 110. The lookup engine 210 performs the lookup task against one or more curated entity-specific dictionaries. The entity-specific dictionaries can be curated from multiple data sources. The data sources may be internal (internal sources) to system 100 or external (external sources) to system 100, or both. The internal sources include data obtained from an electronic medical record (EMR), a disease dictionary, a drug dictionary, a procedure dictionary, or a combination of each. External sources can include websites or information databases managed by government agencies and health organizations, including domestic and international organizations such as the World Health Organization.

The data obtained from the EMR includes information describing healthcare and medical conditions of multiple patients and can be structured data or unstructured data. The disease dictionary can correspond to an ICD-10 disease database, where ICD-10 is a revision of a document that defines the encoding and classification scheme for the International Statistical Classification of Diseases and Related Health Problems (ICD). The procedure dictionary can correspond to a procedure code mapping database for mapping procedure names to respective procedure codes.

The drug dictionary can correspond to a GPI code mapping database for mapping drug names to respective GPI codes. A generic product identifier (GPI) is a 14-character hierarchical classification system that identifies drugs from at least their primary therapeutic use. The drug dictionary can correspond to an ATC code mapping database for mapping pharmaceutical drugs to respective ATC codes of an Anatomical Therapeutic Chemical (ATC) Classification System. The ATC codes are used for the classification of active ingredients of drugs, e.g., according to the organ or system on which they act and their therapeutic, pharmacological, and chemical properties.

Machine-learning (ML) engine 220 is configured to analyze a given portion of text from input data 110 and identify or recognize whether each word or term in the text corresponds to a medical entity. The ML engine can include one or more trained neural networks. The ML engine 220 performs the analysis and term recognition functions using specific computing rules (e.g., ML algorithms) that are derived from neural networks that are trained based on a particular algorithm. An architecture of the neural networks can be a bi-directional LSTM-CRF (Long Short-Term Memory-Conditional Random Fields).

Specific computing rules are derived or learned by the neural networks in response to training the neural networks using one or more datasets, such as "gold-quality" and "silver-quality" datasets. In some implementations, the gold-quality datasets are obtained from one or more of the external data sources described above. The silver quality datasets are generated using the curated entity-specific dictionaries that are also described above. During an implementation phase of system 100, performance of an example data model associated with the ML engine 220 can be further improved using transfer learning. For example, deep learning models may be pre-trained on a different task where a large amount of training data is available or trained in an unsupervised fashion which does not require manually generated training data. Pre-trained models can be fine-tuned (i.e., adapted) to a specific task, based on transfer learning, to improve performance of the models and with a reduced amount of training data. In this manner, models trained to a first task can be more efficiently re-purposed to learning a second-related task based on the inferences learned when processing data related to the first task.

Referring now to encoding module 140, as described above, medical entities are linked or encoded with a specified category based on an encoding scheme for the specified category. Encoding module 140 can include discrete computing elements that are each used to perform the respective encoding operation for either diseases, drugs, or procedures. For example, as shown at FIG. 2, encoding module 140 includes a disease encoder 230, a drug encoder 235, and a procedure encoder 240.

Disease encoder 230 is a discrete computing element used to perform the specific encoding operations for encoding medical entities associated with health-related diseases. Disease encoder 230 is configured to map a given disease name (e.g., a medical entity) into an ICD-10 code. ICD-10 codes provide a standardized nomenclature of disease names and conditions. Category codes 145 for ICD-10 disease encoding is based on an encoding scheme that is hierarchically organized. For example, in the hierarchy of levels, a top level is level 1, a second level is level 2, a third level is level 3, a fourth level is level 4, and a fifth level is level 5. Disease encoder 230 is configured to map or encode medical entities for disease names up to level 5.

Disease encoder 230 includes various data searching/look-up and a machine-learning functions. In particular, entity module 120 includes a data lookup engine 232 and a ML engine 234. In some implementations, the lookup engine 232 and ML engine 234 are independent computing elements of the disease encoder 230. Lookup engine 232 performs a dictionary lookup on medical entities relating to disease names in a curated entity-specific disease dictionary. Lookup engine 232 is configured to retrieve one or more corresponding ICD-10 codes for a given medical entity that matches a particular disease name. In some cases, the entity-specific disease dictionary is curated from data derived from one or more electronic medical records (EMR).

ML engine 234 includes one or more neural networks 150. As indicated above, ML engine 234 can use the neural network(s) 150 to determine a corresponding level for mapping or encoding the data associated with the medical entity. The ML engine 234 determines the corresponding level with reference to the depths of levels (level 1-level 5) in the hierarchy of levels. In some implementations, ML engine 234 includes one neural network model 150 to perform encoding operations for each level (e.g., level 1-5) of ICD-10 nomenclature. A computed inference output (e.g., a similarity score) of the neural network model can be used to associate a medical entity with a particular depth level in the hierarchy of levels and a corresponding category (or subcategory) code 145 for that depth level. For example, ML engine 234 can generate a score for each node (or level) in a disease category tree with respect to a given user query. The category tree can include a parent level and at least one sub-category that corresponds to a child level.

For a given user query ML engine 234 uses the scores to decide whether a certain parent category should be included. For example, for a given disease category 'A' with sub-categories 'A1', 'A2', and 'A3' and user query 'Q', ML engine 234 first generates three respective similarity scores with respect to 'Q': score S1, score S2, and score S3. Each of these scores can correspond to 'A' subcategories. The system 100 determines whether any of the scores is lower than a pre-defined threshold. If at least one score is lower than a pre-defined threshold, the system predicts the sub-categories (A1, A2, etc.) of category 'A' as outputs, whereas if all the scores, S1, S2, etc., are higher than the pre-defined threshold, then the system predicts category 'A' as the output. Algorithm can be trained to predict high similarity scores not only for a query-disease category, but also to all query-disease sub-category levels. Hence, using these methods, system 100 can identify the level as well as a correct code at that level.

In other implementations, ML engine 234 includes five neural network models, where the five neural network models corresponds to neural networks 150. In this implementation, ML engine 234 uses a respective neural network model to perform encoding operations for a particular level (e.g., level 1-5) of ICD-10 nomenclature. A computed inference output of each respective neural network model can be used to associate a medical entity with a particular depth level in the hierarchy of levels and a corresponding category code 145 for that depth level.

For example, each neural network model can compute a confidence score (e.g., an output) that is used to determine best matches for an official disease name and for a specific level in the ICD-10 nomenclature for a given disease name. As an example, for a medical entity "lung cancer," a confidence score from a particular neural network model can indicate that a best matching level 1 ICD-10 official disease name is "Neoplasms," or that best matching level 2 ICD-10 official disease name is "Malignant neoplasms of respiratory and intrathoracic organs." For example, if a confidence score for "Neoplasms" exceeds a confidence score for another disease name (or a threshold score), then the disease encoder 230 determines that the best matching level 1 ICD-10 official disease name is "Neoplasms." In some implementations, the neural network models have the same architecture. For example, the architecture can be based on a siamese recurrent neural network (RNN) with a single output that generates a single confidence/similarity score. In some implementations, each neural network model is trained on one or more existing mappings from a set of EMRs.

Drug encoder 235 is a discrete computing element used to perform the specific encoding operations for encoding medical entities associated with pharmaceutical drugs. Drug encoder 235 can be configured to retrieve matching GPI-10 codes for a given medical entity that matches a generic or drug product name. Drug encoder 235 can also be configured to retrieve matching ATC codes for a given medical entity that matches a generic or drug product name. In some implementations, the mapping or encoding is performed based on an exact and fuzzy search against data entries of a curated entity-specific drug dictionary. The drug dictionary can include a listing of GPI-10 codes, drug product names, generic drug product names, and ATC codes, including data relating to active ingredients and chemical properties of different pharmaceutical drugs. In some cases, the drug dictionary is curated using an example internal GPI-10-generic name mapping dictionary or ATC code mapping dictionary.

Procedure encoder 240 is a discrete computing element used to perform the specific encoding operations for encoding medical entities associated with medical procedures. Procedure encoder 240 is configured to retrieve matching PRC_CD codes for a given medical entity that matches a particular procedure name (e.g., a medical procedure). In some implementations, the mapping or encoding is performed based on an exact and fuzzy search against data entries of a curated entity-specific procedure dictionary. The procedure dictionary can include a listing of procedure codes (PRC_CD) and procedure names. In some cases, the procedure dictionary is curated using an example internal PRC_CD—Procedure name mapping dictionary.

Encoding module 140 can also include one or more additional encoders 245. For example, the additional encoders 245 can be used to encode data describing medical findings that are associated with patient signs and symptoms, a patient's vitals, a patient's lab test results (e.g., BMI or cholesterol numbers). In some implementations, the additional encoders 245 can be used to encode data describing temporal entities that may be associated with the medical findings. For example, the temporal entities can indicate whether a medical finding was obtained or determined within the last month, the last year, or two years ago. In other implementations, the additional encoders 245 can be used to encode data as identifying an age group to which a patient belongs, e.g., adult, neonate, greater than 18 years old, or as identifying a genetic marker, e.g., cancer or another abnormality due to specific genetic mutation.

As indicated above, encoding module 120 and encoding module 140 interact to execute a variety of data processing and signal processing functions that define a training phase 155 of system 100. Execution of these functions enable completion of the training phase 155 such that system 100 can generate a trained predictive model 160.

During the training phase 155, lookup engine 210 performs a search of data elements in the input data 110 against the curated entity-specific dictionaries. For example, lookup engine 210 is configured to extract one or more single words (e.g., unigrams), extract two consecutive words (e.g., bigrams), or extract three consecutive words (e.g., trigrams). In some implementations, the lookup engine 210 extracts the unigrams, bigrams, and trigrams in sequential order so that the unigrams are extracted first, the bigrams are extracted second, and the trigrams are extracted third. In other implementations, the lookup engine 210 extracts the unigrams, bigrams, and trigrams (collectively "n-grams") in no particular order.

The extracted n-grams are matched against the curated entity-specific dictionaries in an exact match mode or fuzzy mode. During an implementation phase of the system 100, e.g., that uses a trained predictive model 160, extracted n-grams are matched against the curated entity-specific dictionaries in a fuzzy mode. In some implementations, the fuzzy mode matching is based on an example minimum-edit-distance algorithm. For example, if the lookup engine 210 detects a match between an input term/word or phrase and an entity in a specific dictionary, then the particular matching word or phrase is labelled with the corresponding matching medical entity.

Parsing engine 170 is a semantic query parser that is configured to convert user input 125 to a machine-readable command. As described in more detail below, based on a received query, the parsing engine 170 is generally configured: i) to perform named entity recognition to extract patient attributes from the query; ii) encode one or more patient attributes into a standard format; iii) if multiple patient attributes are mentioned, then determine how one or more of the attributes should be combined; iv) determine if any of the patient attribute criteria should be negated; and v) based on the outcome of one or more of the preceding steps i)-iv), build a computer understandable query searching a medical database 190. Parsing engine 170 includes name entity recognition (NER) and encoding engine 250, entity negation engine 255, and conjunction engine 260. For a given query input, NER and encoding engine 250 is configured to identify all patient attributes that are related to one or more medical concepts, patient diagnosis, patient prescription history, and medical procedures that previously provided to the patient. Entity negation engine 255 can include software instructions for a negation identifier that identifies whether to include or exclude certain patient attributes.

Conjunction engine 260 can include software instructions for identifying conjunction patterns in a query input. For example, when multiple patient attributes are queried, conjunction engine 260 can identify one or more conjunction patterns in an example user input. As an example, conjunction engine 260 is configured to differentiate between the following two queries: i) "patients with fever AND pain" vs. ii) "patients with fever OR pain." Conjunction engine 260 is configured to differentiate between the first and second queries based on an identified conjunction pattern of each query. For example, in the first query i), both "fever" and "pain" attributes must be present, whereas in the second query ii), the existence of either attribute is sufficient.

Figure 3:
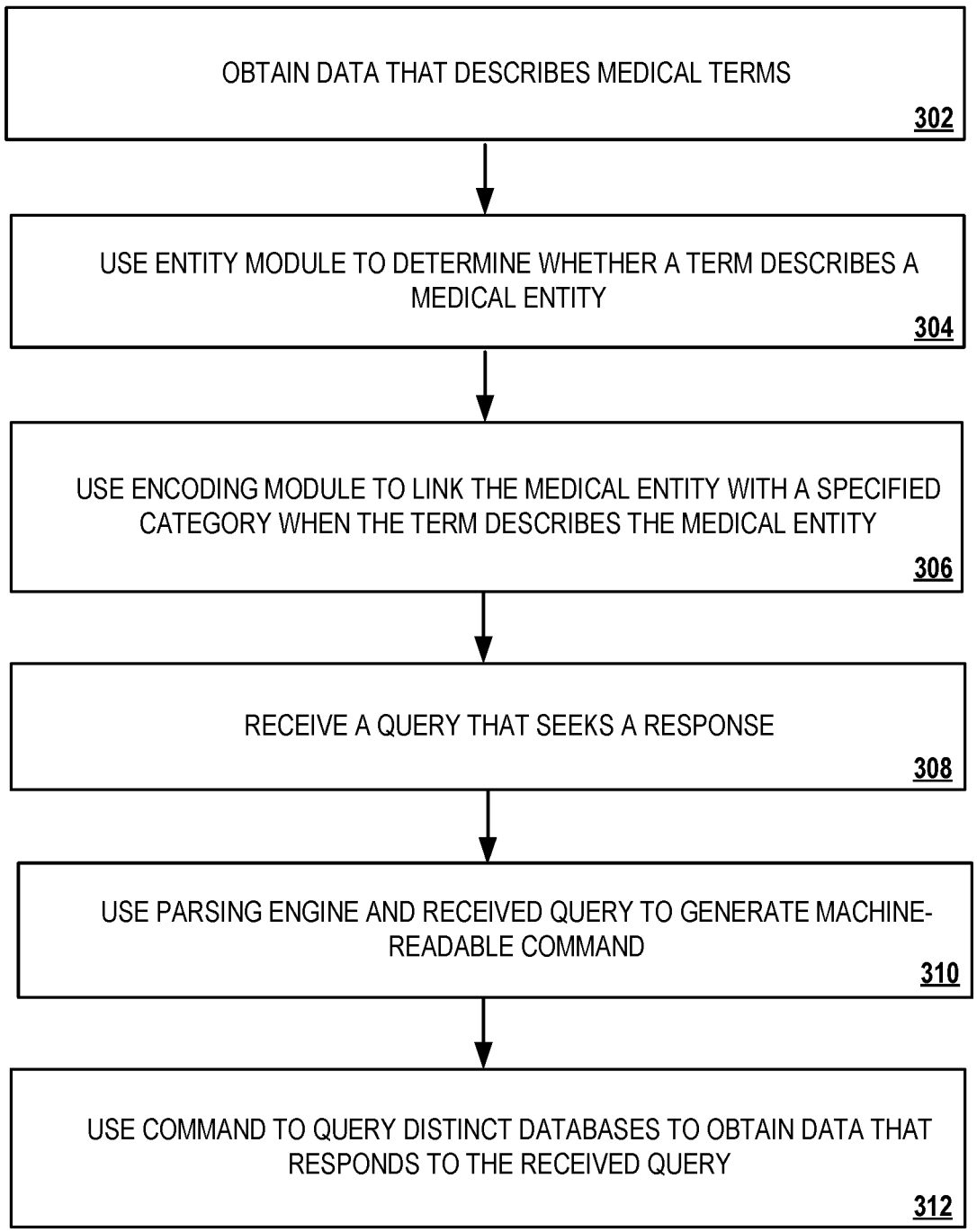
FIG. 3 is an example process for generating machine-readable commands using a predictive model of the computing system of FIG. 1.

FIG. 3 is an example process 300 for generating a machine-readable command based on the described techniques. Process 300 can be implemented using one or more computing elements of system 100 described above as well as other components and instructions described in this document.

Referring now to process 300, system 100 obtains data that describes terms relating to multiple different medical concepts (302). In some implementations, the obtained data is structured or unstructured data included in the input data 110. For example, the unstructured data 202 includes healthcare transaction information obtained from data describing interactions between physicians and patients, data derived from a subject's physical or electronic medical records (EMR), data derived from prescription records/medical claims ("Rx/Dx data"), or data relating to prescriptions or treatment options used by a patient or subject.

The system 100 uses an entity module to determine whether a term describes a medical entity (304). The medical entity can be associated with a healthcare condition that affects an individual. For example, during a training phase 155 of system 100, entity module 120 performs a dictionary look-up of each word or term in a medical document or unstructured data source, such as a patient EMR. The medical document can have letters that form words that describe a particular medical condition, such as cancer (e.g., a medical entity). The terms or words that describe, or are associated with, a medical entity are extracted when the entity module 120 detects that the words match terms in the curated data source that also describe medical concepts related to cancer.

During an implementation phase of system 100, determining whether a term describes a medical entity can include the predictive model 160 computing inferences for determining a confidence that a term, e.g., in user input 125, is relevant to describing a medical entity, such as cancer. The predictive model 160 cam generate a confidence score that represents a confidence that the term describes the medical entity. For example, a query can be "show a listing of patients that are in chemotherapy?" The predictive model 160 can determine that the term "chemotherapy" describes the medical entity, cancer, based on a confidence score that exceeds a threshold confidence score.

The system 100 uses an encoding module to link the medical entity with a specified category (306). For example, during at least the training phase 155, when the term recognized in the input data 110 describes the medical entity the encoding module 140 is used to link the medical entity with the specified category. The medical entity is linked or encoded with the specified category based on an encoding scheme for the specified category. For example, the encoding module 140 obtains a listing of category codes 145 for the specified category and determines a match between the term that describes the medical entity and corresponding one or more category codes in the listing of category codes. The encoding module 140 then links the medical entity with the specified category based on the determined match between the term that describes the medical entity and the corresponding category codes.

In some implementations, the encoding scheme for the specified category is a hierarchical encoding scheme that includes a hierarchy of levels. In this implementation, encoding the medical entity with the corresponding category codes includes: i) quantifying information content that includes the medical entity to be encoded; ii) determining depths of levels in the hierarchy of levels for mapping the information content; and iii) associating the medical entity included in the information content with the corresponding category codes for a particular depth level in the hierarchy of levels. Quantifying information content can include the task of identifying a correct category level for a given query. For example, in the case of disease encoding, the term "infection" may not contain sufficient information to map a medical entity to a specific type of infection, such as mapping it to "tuberculosis of lungs." So, in this case, the system 100 can map "infection" to a highest category of diseases that contain all "infections," as described above with reference to computing similarity scores for a given category tree.

The predictive computing system 100 receives a query that seeks a response (308). For example, the query can be a request for a list of subjects that are suitable candidates for participation in a clinical trial that evaluates the efficacy of a new cancer treatment drug. The parsing engine 170 of system 100 uses the received query to generate a machine-readable command (310). In some implementations, the command is generated in response to the parsing engine 170 parsing the query against terms that describe the medical entity and based on the encoding scheme for linking the medical entity to the specified category.

The parsing engine 170 can perform the query parsing operations to determine types of relationships between terms based on certain keywords in the user input 125, a certain position of words in the text of the user input 125, or semantic attributes of terms that form the user input 125. In some implementations, the parsing engine 170 uses one or more semantic parsing functions to determine the semantic attributes of the terms in the user input 125. The semantic parsing functions can include extracting a sentence syntax from the user input 125, e.g., by applying specific computing rules derived from a machine-learning solution that may be pre-trained to detect sentence syntax of an input phrase or query.

The system 100 uses the command to query one or more databases to obtain data for generating a response to the received query (312). For example, the trained predictive model 160 can interact with the entity module 120 and the encoding module 140 to identify one or more patient attributes as conditions, e.g., health-related or medical conditions. The semantic parsing functions of the parsing engine 170 can be used to determine: (1) whether each condition is negated; and (2) when more than one condition is specified, what relationship(s) exists between different conditions. For example, relationships that exist between different conditions can be determined, or defined, using one or more logic operands, such as a logic AND operation, a logic OR operation, or a logic NOT operation.

Figure 4:
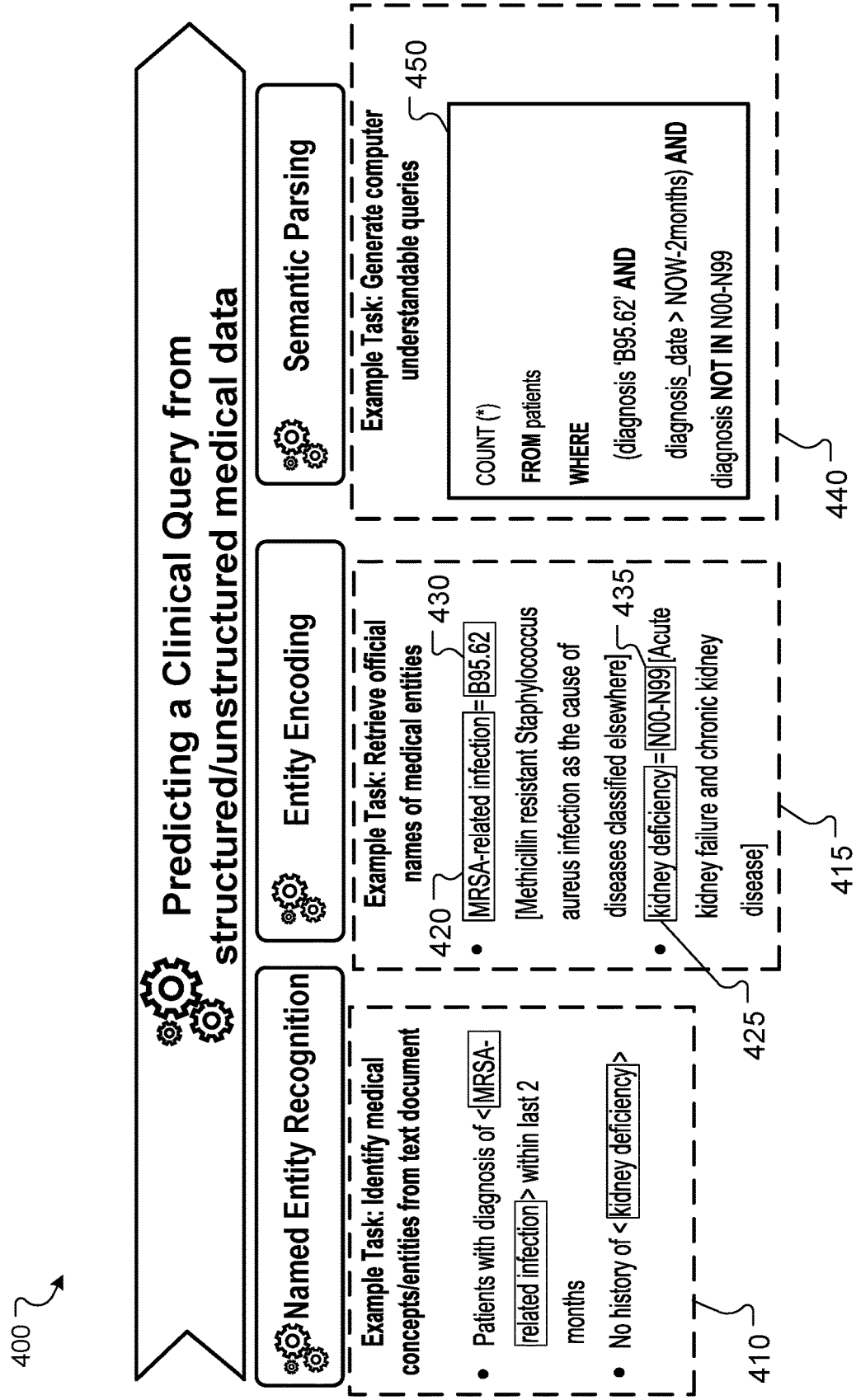
FIG. 4 shows an example data flow for processing unstructured medical data to generate machine-understandable queries.

FIG. 4 shows an example data flow 400 for processing structured and unstructured medical data that may be included in the input data 110. Similar to process 300 described above, data flow 400 can be implemented using one or more computing elements of system 100 described above as well as other components and instructions described in this document.

Referring now to dataflow 400, system 100 uses the entity module 120 to perform the example task of identifying medical concepts or medical entities included in a text document (410). For example, the text document can be a medical journal or text included in unstructured data 202, such as an EMR of a patient. As shown, the identified text may be one or more terms that are identified within a larger group of terms, words, or phrases. This larger group of terms may identify a particular patient that had a certain type of medical diagnosis within the last two years. In one implementation, the larger group of terms may also state that the patient has "no history of <kidney deficiency>." In some cases, the identified text for the particular patient is unstructured data 202 obtained from an EMR for the patient, e.g., during a training phase 155 of system 100. In the implementation of FIG. 4, the one or more terms identified by the entity module 120 include "MRSA-related infection" and "kidney deficiency."

Using the techniques described above, the entity module 120 interacts with the encoding module 140 to retrieve official names of one or more medical entities that are described by the identified terms (415). For example, the entity module 120 determines that the identified terms describe or relate to the medical entity 420, Methicillin-resistant *Staphylococcus aureus* (MRSA), which is a *bacterium* that causes infections in different parts of the body. The entity module 120 also determines that the identified terms describe or relate to the medical entity 425, "kidney deficiency," which may correspond to other medical concepts or entities including acute kidney failure or chronic kidney disease.

For example, the entity module 120 determining that the one or more terms describe the medical entities 420, 425 includes: i) performing, using the lookup engine 210 or ML engine 220, a lookup of the larger group of terms against information in a curated entity-specific dataset; ii) determining a match between the one or more terms and the information in the curated entity specific dataset; and iii) determining that the one or more terms describe medical entities 420, 425 based on a determined match between the one or more terms and the information in the curated entity specific dataset.

The encoding module 140 uses at least one of the encoders 230, 235, 240, 245 to retrieve the official names of one or more medical entities 420, 425 that are described by the identified terms. For example, the encoding module 140 can use lookup engine 232, or ML engine 234, of the disease encoder 230 to perform a dictionary lookup on medical entities relating to disease names in a curated entity-specific disease dictionary. Each of lookup engine 232 and ML engine 234 are configured to retrieve: i) corresponding ICD-10 codes 430, for medical entity 420, which matches a particular disease name; and ii) corresponding ICD-10 codes 435, for medical entity 425, which matches a particular disease name.

Retrieving the official disease names associated with the one or more terms can include linking, using the encoding module 140, the medical entities 420, 425 with a specified category when the one or more terms describe the medical entities 420, 425. The medical entities 420, 425 are linked with the specified category based on an encoding scheme for the specified category.

In general, the medical entities 420, 425 can include at least one of: a) medical diseases that are related to a particular medical concept; b) medical drugs for treating medical diseases that are related to the particular medical concept; c) medical procedures associated with medical diseases that are related to the particular medical concept; or d) data describing multiple medical findings that correspond to a healthcare or medical condition of a patient.

In some implementations, the curated entity specific datasets are generated based on data including one or more of: i) a predefined set of information that describes multiple types of diseases, e.g., the curated entity-specific disease dictionary described above; ii) a predefined set of information that describes multiple pharmaceutical drugs, e.g., the curated entity-specific drug dictionary described above; iii) a predefined set of information that describes multiple medical procedures, e.g., the curated entity-specific procedure dictionary described above; or iv) electronic medical data for multiple healthcare patients, e.g., the patient EMR data described above.

Using the techniques described above, the parsing engine 170 interacts with the predictive model 160 to generate computer understandable queries (440). For example, the parsing engine 170 uses a received query 125 to generate a machine-readable command 450. The query 125 can be a user query that states "show me patients that had a diagnosis of <MRSA related infection> within the last 2 months and that have no history of <kidney deficiency>." In some implementations, the command is generated by parsing the query against terms that describe the medial entity and based on the encoding scheme for linking the medical entity to the specified category.

For the example query input 125, the parsing engine 170 uses the NER and encoding engine 250 to identify all patient attributes related to the patient's diagnosis and medical history. A negation identifier of the entity negation engine 255 is used to identify whether to include or exclude certain patient attributes. For example, the entity negation module 255 can cause that the generated command to be structured such that patients with a history of kidney deficiency are excluded from a database search, e.g., by including the sub-command "diagnosis NOT IN N00-N99," where "N00-N99" corresponds to an example ICD-10 category code for acute kidney failure or chronic kidney disease.

The conjunction engine 260 is used to identify conjunction patterns in the query input. For example, as indicated above, when multiple patient attributes are queried, the conjunction engine 260 identifies conjunction patterns in an example user input/query 125. Hence, the conjunction engine 260 is configured to identify the "and" conjunction in the query 125. In this manner, the parsing engine 170 can generate a machine-readable command 450 that obtains, from a patient database, a listing of patients that have patient attributes indicating a diagnosis for disease category code B95.62 (MSRA-related infections) AND with a diagnosis date that ranges from NOW (current date) to the past 2-months. The machine-readable command 450 can also include a negation sub-command to cause the database search to return patients that have diagnosed conditions which are NOT IN disease category code "N00-N99."

Figure 5:
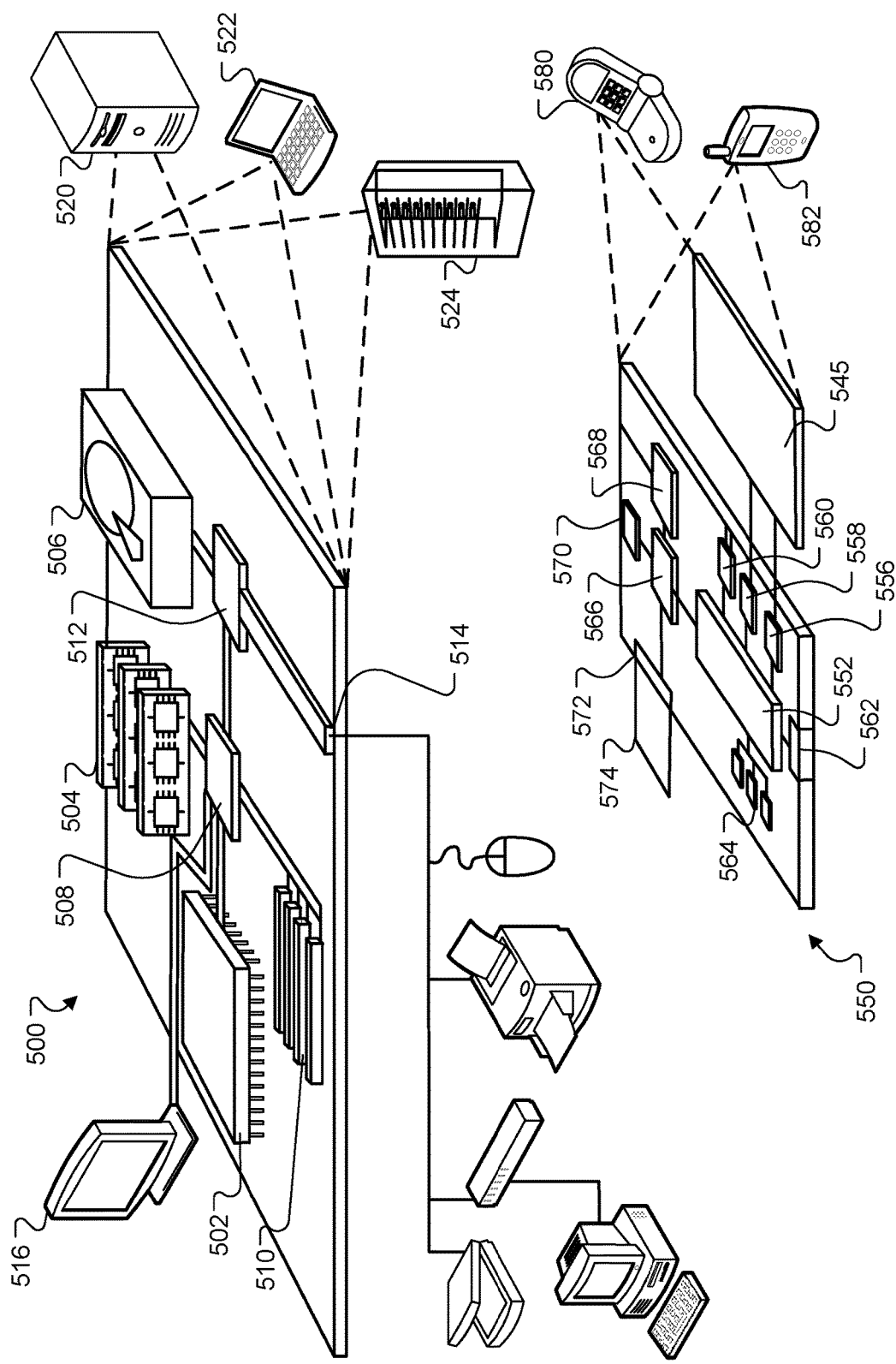
FIG. 5 shows a block diagram of a computing system that can be used in connection with methods described in this document.

FIG. 5 is a block diagram of computing devices 500, 550 that may be used to implement the systems and methods described in this document, as either a client or as a server or multiple servers. Computing device 500 and 550 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations, e.g., as a server bank, a group of blade servers, or a multi-processor system.

The memory 504 stores information within the computing device 500. In one implementation, the memory 504 is a computer-readable medium. In one implementation, the memory 504 is a volatile memory unit or units. In another implementation, the memory 504 is a non-volatile memory unit or units.

The storage device 506 is capable of providing mass storage for the computing device 500. In one implementation, the storage device 506 is a computer-readable medium. In various different implementations, the storage device 506 may be a floppy disk device, a hard disk device, an optical disk device, or a tape device, a flash memory or other similar solid-state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 504, the storage device 506, or memory on processor 502.

The high-speed controller 508 manages bandwidth-intensive operations for the computing device 500, while the low speed controller 512 manages lower bandwidth-intensive operations. Such allocation of duties is exemplary only. In one implementation, the high-speed controller 508 is coupled to memory 504, display 516, e.g., through a graphics processor or accelerator, and to high-speed expansion ports 510, which may accept various expansion cards (not shown). In the implementation, low-speed controller 512 is coupled to storage device 506 and low-speed expansion port 514. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can process instructions for execution within the computing device 550, including instructions stored in the memory 564. The processor may also include separate analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD display or an OLED display, or other appropriate display technology. The display interface 556 may include appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication, e.g., via a docking procedure, or for wireless communication, e.g., via Bluetooth or other such technologies.

The memory 564 stores information within the computing device 550. In one implementation, the memory 564 is a computer-readable medium. In one implementation, the memory 564 is a volatile memory unit or units. In another implementation, the memory 564 is a non-volatile memory unit or units. Expansion memory 574 may also be provided and connected to device 550 through expansion interface 572, which may include, for example, a SIMM card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provided as a security module for device 550, and may be programmed with instructions that permit secure use of device 550. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS receiver module 570 may provide additional wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound, e.g., voice messages, music files, etc., and may also include sound generated by applications operating on device 550.

The computing device 550 may be implemented in a number of different forms, as shown in the figure. For example, it may be implemented as a cellular telephone 580. It may also be implemented as part of a smartphone 582, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

What is claimed is:

1. A computer-implemented method performed using a system, the method comprising:
   obtaining data comprising a plurality of terms;
   determining that a term of the plurality of terms describes a medical entity;
   determining, by a predictive model of the system, a respective confidence score between each term of the plurality of terms and the medical entity;
   linking, by an encoding module that interacts with the predictive model, the medical entity with a category from categories of medical information based on an encoding scheme for the category and the confidence score associated with the term, wherein the encoding module performs the linking by employing one or more machine learning models to associate the medical entity with the category for a particular depth level in a hierarchical encoding scheme comprising a hierarchy of levels;
   responsive to receiving a query, generating a machine-readable command at least by parsing the query against information about the medical entity linked to the category based on the encoding scheme and the confidence score;
   generating a reply to the query after using the machine-readable command to query one or more databases; and
   providing the reply as an output for display at a user device.

2. The method of claim 1, wherein determining whether a term describes the medical entity comprises:
   determining the confidence score exceeds a threshold confidence score.

3. The method of claim 1, wherein linking the medical entity with the category comprises:
   obtaining a listing of category codes for the category;
   determining a match between the term and corresponding category codes in the listing of category codes; and
   linking the medical entity with the category based on the match between the term that describes the medical entity and the corresponding category codes.

4. The method of claim 1, wherein linking the medical entity with the category comprises:
   encoding the medical entity with corresponding category codes based on the encoding scheme for the category; and
   wherein the encoding scheme for the category is the hierarchical encoding scheme comprising the hierarchy of levels.

5. The method of claim 4, wherein encoding the medical entity with corresponding category codes includes:
   quantifying content comprising the medical entity to be encoded;
   determining depths of levels in the hierarchy of levels for mapping the content; and
   associating the medical entity included in the content with the corresponding category codes for a particular depth level in the hierarchy of levels.

6. The method of claim 4, wherein the medical entity is a disease, and determining the match comprises:
   generating a respective match score for each level in the hierarchy of levels; and
   determining that the respective match score exceeds a threshold match score.

7. The method of claim 1, wherein determining that the term describes the medical entity comprises:
   performing a lookup of the term against information in an entity-specific dataset; and
   determining that the term describes the medical entity based on a match between the term and a first entry in the entity-specific dataset.

8. The method of claim 7, wherein the medical entity is associated with a healthcare condition that affects an individual, and wherein the medical entity comprises at least one of:
   one or more medical diseases;
   medical drugs for treating the one or more medical diseases;
   medical procedures associated with the one or more medical diseases; or
   data describing a plurality of medical findings that correspond to a healthcare condition of the individual.

9. The method of claim 7, wherein the entity specific dataset is generated based on data including at least one of:
   i) a predefined set of information describing a plurality of diseases;
   ii) a predefined set of information describing a plurality of drugs;
   iii) a predefined set of information describing a plurality of medical procedures; or
   iv) electronic medical data for a plurality of healthcare patients.

10. The method of claim 1, wherein obtaining the data that describes the terms relating to a plurality of medical concepts comprises:
    obtaining a plurality of unstructured data; and
    structuring the unstructured data to enable processing of the query against information in multiple databases of the system.

11. A system, comprising:
    one or more processing devices; and
    one or more non-transitory machine-readable storage devices storing instructions that are executable by the one or more processing devices to cause performance of operations comprising:

obtaining data comprising a plurality of terms;
determining that a term of the plurality of terms describes a medical entity;
determining, by a predictive model of the system, a respective confidence score between each term of the plurality of terms and the medical entity;
linking, by an encoding module that interacts with the predictive model, the medical entity with a category from categories of medical information based on an encoding scheme for the category and the confidence score associated with the term, wherein the encoding module performs the linking by employing one or more machine learning models to associate the medical entity with the category for a particular depth level in a hierarchical encoding scheme comprising a hierarchy of levels;
responsive to receiving a query, generating a machine-readable command at least by parsing the query against information about the medical entity linked to the category based on the encoding scheme and the confidence score;
generating a reply to the query after using the machine-readable command to query one or more databases; and
providing the reply as an output for display at a user device.

12. The system of claim 11, wherein determining whether a term describes the medical entity comprises:
determining the confidence score exceeds a threshold confidence score.

13. The system of claim 11, wherein linking the medical entity with the category comprises:
obtaining a listing of category codes for the category;
determining a match between the term and corresponding category codes in the listing of category codes; and
linking the medical entity with the category based on the match between the term that describes the medical entity and the corresponding category codes.

14. The system of claim 11, wherein linking the medical entity with the category comprises:
encoding the medical entity with corresponding category codes based on the encoding scheme for the category; and
wherein the encoding scheme for the category is the hierarchical encoding scheme comprising the hierarchy of levels.

15. The system of claim 14, wherein encoding the medical entity with corresponding category codes includes:
quantifying content comprising the medical entity to be encoded;
determining depths of levels in the hierarchy of levels for mapping the content; and
associating the medical entity included in the content with corresponding category codes for a particular depth level in the hierarchy of levels.

16. The system of claim 14, wherein the medical entity is a disease, and determining the match comprises:
generating a respective match score for each level in the hierarchy of levels; and
determining that the respective match score exceeds a threshold match score.

17. The system of claim 11, wherein determining that the term describes the medical entity comprises:
performing a lookup of the term against information in an entity-specific dataset; and
determining that the term describes the medical entity based on a match between the term and a first entry in the entity-specific dataset.

18. The system of claim 17, wherein the medical entity is associated with a healthcare condition that affects an individual, and wherein the medical entity comprises at least one of:
one or more medical diseases;
medical drugs for treating the one or more medical diseases;
medical procedures associated with the one or more medical diseases; or
data describing a plurality of medical findings that correspond to a healthcare condition of the individual.

19. The system of claim 11, wherein obtaining the data that describes the terms relating to a plurality of medical concepts comprises:
obtaining a plurality of unstructured data; and
structuring the unstructured data to enable processing of the query against information in multiple databases of the system.

20. One or more non-transitory machine-readable storage devices storing instructions that are executable by one or more processing devices to cause performance of operations comprising:
obtaining data comprising a plurality of terms;
determining that a term of the plurality of terms describes a medical entity;
determining, by a predictive model of the system, a respective confidence score between each term of the plurality of terms and the medical entity;
linking, by an encoding module that interacts with the predictive model, the medical entity with a category from categories of medical information based on an encoding scheme for the category and the confidence score associated with the term, wherein the encoding module performs the linking by employing one or more machine learning models to associate the medical entity with the category for a particular depth level in a hierarchical encoding scheme comprising a hierarchy of levels;
responsive to receiving a query, generating a machine-readable command at least by parsing the query against information about the medical entity linked to the category based on the encoding scheme and the confidence score;
generating a reply to the query after using the machine-readable command to query one or more databases; and
providing the reply as an output for display at a user device.

* * * * *